(12) United States Patent
Otsuka et al.

(10) Patent No.: US 11,378,515 B2
(45) Date of Patent: Jul. 5, 2022

(54) IMAGE PROCESSING DEVICE, IMAGING SYSTEM, ACTUATION METHOD OF IMAGE PROCESSING DEVICE, AND COMPUTER-READABLE RECORDING MEDIUM

(71) Applicant: OLYMPUS CORPORATION, Tokyo (JP)

(72) Inventors: Takeshi Otsuka, Tokyo (JP); Kunio Hori, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 16 days.

(21) Appl. No.: 17/152,382

(22) Filed: Jan. 19, 2021

(65) Prior Publication Data
US 2021/0164904 A1 Jun. 3, 2021

Related U.S. Application Data

(63) Continuation of application No. PCT/JP2018/030987, filed on Aug. 22, 2018.

(51) Int. Cl.
*G01N 21/64* (2006.01)
*G02B 21/00* (2006.01)
(Continued)

(52) U.S. Cl.
CPC ..... *G01N 21/6428* (2013.01); *G01N 21/6458* (2013.01); *G02B 21/0076* (2013.01);
(Continued)

(58) Field of Classification Search
CPC ........... G01N 21/6428; G01N 21/6458; G01N 33/48; G01N 2021/6439; G02B 21/0076;
(Continued)

(56) References Cited

U.S. PATENT DOCUMENTS 6,169,816 B1 * 1/2001 Ravkin .............. G01N 15/1475
382/128
8,244,021 B2 * 8/2012 Lett ..................... G06F 3/04847
382/128
(Continued)

FOREIGN PATENT DOCUMENTS

JP 2010-512508 A 4/2010
JP 2014-526700 A 10/2014
(Continued)

OTHER PUBLICATIONS

International Search Report dated Nov. 20, 2018 issued in PCT/JP2018/030987.
(Continued)

*Primary Examiner* — David P Porta
*Assistant Examiner* — Djura Malevic
(74) *Attorney, Agent, or Firm* — Scully, Scott, Murphy & Presser, P.C.

(57) ABSTRACT

An image processing device includes: a processor including hardware. The processor is configured to: with respect to each pixel included in a fluorescent image obtained by capturing a tissue group including one or more tissues dyed by using a fluorescent dye group including one or more fluorescent dyes by a fluorescent microscope, estimate a light quantity of fluorescence emitted by each fluorescent dye of the fluorescent dye group; estimate a tissue amount of each tissue of the tissue group based on the estimated light quantity; estimate a virtual dye amount of each dye of a bright-field dye group of a case in which the tissue group dyed by using the bright-field dye group including one or more dyes is captured by a transmission-type microscope based on the estimated tissue amount; and generate a virtual transmitted-light image from the estimated dye amount.

10 Claims, 7 Drawing Sheets

(51) Int. Cl.
*G02B 21/12* (2006.01)
*G02B 21/36* (2006.01)

(52) U.S. Cl.
CPC ........... *G02B 21/12* (2013.01); *G02B 21/365* (2013.01); *G01N 2021/6439* (2013.01)

(58) Field of Classification Search
CPC .................. G02B 21/12; G02B 21/365; G06T 2207/30024; G06T 5/008; G06T 2207/10056; G06T 2207/30242; A61B 1/043; C12M 1/34
See application file for complete search history.

(56) References Cited

U.S. PATENT DOCUMENTS

| | | | |
|---|---|---|---|
| 8,290,235 B2* | 10/2012 | Lett | G01N 21/6428 382/128 |
| 8,639,013 B2* | 1/2014 | Kenny | G01N 21/6458 382/162 |
| 9,329,130 B2* | 5/2016 | Chan | G01N 21/6458 |
| 9,541,504 B2* | 1/2017 | Hoyt | G06V 20/695 |
| 9,697,582 B2* | 7/2017 | Grunkin | G06T 7/0012 |
| 2008/0212866 A1 | 9/2008 | Lett et al. | |
| 2008/0317325 A1* | 12/2008 | Ortyn | G01N 15/147 382/133 |
| 2011/0235879 A1* | 9/2011 | Lett | G06F 3/04842 382/128 |
| 2012/0076390 A1* | 3/2012 | Potts | G06T 7/38 382/133 |
| 2012/0200694 A1* | 8/2012 | Garsha | G01N 21/6456 382/128 |
| 2013/0044933 A1* | 2/2013 | Kenny | G01N 21/643 382/133 |
| 2015/0065371 A1* | 3/2015 | Seppo | C12Q 1/6886 506/9 |
| 2015/0105283 A1* | 4/2015 | Weiss | G01N 33/582 506/18 |
| 2017/0176336 A1* | 6/2017 | Dimitriadis | G01J 3/32 |
| 2020/0327657 A1 | 10/2020 | Klaiman et al. | |
| 2022/0087930 A1* | 3/2022 | Gambotto | A61K 39/39 |

FOREIGN PATENT DOCUMENTS

| | | |
|---|---|---|
| JP | 2015-514212 A | 5/2015 |
| JP | 2014-521979 A | 8/2015 |
| WO | WO 2008/133666 A2 | 11/2008 |
| WO | WO 2013/024115 A1 | 2/2013 |
| WO | WO 2013/040300 A2 | 3/2013 |
| WO | WO 2013/148448 A1 | 10/2013 |
| WO | WO 2017/212055 A1 | 12/2017 |

OTHER PUBLICATIONS

Fereidouni, Farzad et al., "Microscopy with UV Surface Excitation (MUSE) for slide-free histology and pathology imaging", Proc. of SPIE (2015), vol. 9318.

* cited by examiner

FIG.4

| | | TISSUE AMOUNT | |
|---|---|---|---|
| | | CELL NUCLEI | CYTOPLASM |
| LIGHT QUANTITY OF FLUORESCENCE | HOECHST | 1.00 | 0.00 |
| | EOSIN | 0.00 | 1.00 |

FIG.5

| | | TISSUE AMOUNT | |
|---|---|---|---|
| | | CELL NUCLEI | CYTOPLASM |
| DYE AMOUNT | HEMATOXYLIN | 1.50 | 0.15 |
| | EOSIN | 2.00 | 2.00 |

IMAGE PROCESSING DEVICE, IMAGING SYSTEM, ACTUATION METHOD OF IMAGE PROCESSING DEVICE, AND COMPUTER-READABLE RECORDING MEDIUM

CROSS-REFERENCE TO RELATED APPLICATION

This application is a continuation of International Application No. PCT/JP2018/030987, filed on Aug. 22, 2018, the entire contents of which are incorporated herein by reference.

BACKGROUND

1. Technical Field

The present disclosure relates to an image processing device, an imaging system, an actuation method of the image processing device, and a computer-readable recording medium.

2. Related Art

In pathological diagnosis, a pathological specimen is prepared by subjecting a specimen isolated from a patient to treatment such as cutting, fixing, embedding, slicing, dying, sealing, etc. Then, the pathological specimen is observed by a microscope, and the presence/absence and degree of illness are diagnosed from the shapes of tissues and dyed states.

As observation by a microscope, transmitted-light observation in which a pathological specimen is irradiated with light and the light transmitted through the pathological specimen is magnified and observed is used. Also, initial diagnosis by subjecting a pathological specimen dyed with hematoxylin eosin (HE) to transmitted-light observation has been carried out. In HE dyeing, tissues such as cell nuclei and bone tissues are dyed bluish purple, and tissues such as cytoplasm, connective tissues, and red blood cells are dyed red. Then, the presence/absence of illness is morphologically diagnosed by observing the shapes of the dyed tissues. Note that the transmitted-light observation is not suitable for observation of a thick specimen since attenuation of light is observed.

Also, as observation by a microscope, fluorescence observation of irradiating a specimen dyed with a fluorescent dye with excitation light and magnifying and observing the fluorescence emitted by the specimen by a fluorescent microscope is used. Since emission of light is observed in the fluorescence observation, a specimen which is thicker than that of the transmitted-light observation can be observed.

A pathological specimen can be imaged by image capturing by connecting a camera to a microscope. Also, in a virtual microscope system (virtual slide system), a whole pathological specimen can be imaged. By imaging the pathological specimen, the image can be used for education, telepathology, etc.

Furthermore, a method of assisting diagnosis by subjecting a pathological specimen image to image processing has been developed. The diagnosis assist includes a method of imitating diagnosis of pathologists by image processing and a method of carrying out machine learning by using a large amount of teaching data. The machine learning uses linear discrimination, deep learning, etc. In pathological diagnosis, the load on pathologists is large due to, for example, lack of pathologists. Therefore, it is expected to reduce the load on pathologists by the diagnosis assist.

As image processing for pathological specimen images, for example, JP 2014-526700 A proposes a method in which dye images in which special dyes or the like are virtually different by subjecting a HE dye image to image processing.

As described above, a thick specimen is not suitable for transmitted-light observation, but can be observed by fluorescence observation. Therefore, if a virtual transmitted-light image can be generated by subjecting a fluorescent image to image processing, a thick specimen can be virtually subjected to transmitted-light observation. For example, "Microscopy with UV Surface Excitation (MUSE) for slide-free histology and pathology imaging", Farzad Fereidouni, Ananya Datta-Mitra, Stavros Demos and Richard Levenson, SPIE Vol. 9318 has proposed a method of generating a virtual transmitted-light image by subjecting a fluorescent image, which has been obtained by capturing a thick specimen, to image processing.

SUMMARY

In some embodiments, an image processing device includes: a processor including hardware. The processor is configured to: with respect to each pixel included in a fluorescent image obtained by capturing a tissue group including one or more tissues dyed by using a fluorescent dye group including one or more fluorescent dyes by a fluorescent microscope, estimate a light quantity of fluorescence emitted by each fluorescent dye of the fluorescent dye group; estimate a tissue amount of each tissue of the tissue group based on the estimated light quantity; estimate a virtual dye amount of each dye of a bright-field dye group of a case in which the tissue group dyed by using the bright-field dye group including one or more dyes is captured by a transmission-type microscope based on the estimated tissue amount; and generate a virtual transmitted-light image from the estimated dye amount.

In some embodiments, an imaging system includes: the image processing device; an illuminator configured to generate excitation light irradiating a specimen; an illumination-light optical system configured to illuminate the specimen with the excitation light generated by the illuminator; an image-forming optical system configured to form an image of the fluorescence from the specimen; and an imager configured to capture the image of the fluorescence formed by the image-forming optical system.

In some embodiments, provided is an actuation method of an image processing device. The actuation method includes: with respect to each pixel included in a fluorescent image obtained by capturing a tissue group including one or more tissues dyed by using a fluorescent dye group including one or more fluorescent dyes by a fluorescent microscope, estimating a light quantity of fluorescence emitted by each fluorescent dye of the fluorescent dye group; estimating a tissue amount of each tissue of the tissue group based on the estimated light quantity; estimating a virtual dye amount of each dye of a bright-field dye group of a case in which the tissue group dyed by using the bright-field dye group including one or more dyes is captured by a transmission-type microscope based on the estimated tissue amount; and generating a virtual transmitted-light image from the estimated dye amount.

In some embodiments, provided is a non-transitory computer-readable recording medium with an executable program stored thereon. The program causes an image processing device to execute: with respect to each pixel included in a fluorescent image obtained by capturing a tissue group including one or more tissues dyed by using a fluorescent dye group including one or more fluorescent dyes by a fluorescent microscope, estimating a light quantity of fluorescence emitted by each fluorescent dye of the fluorescent dye group; estimating a tissue amount of each tissue of the tissue group based on the estimated light quantity; estimating a virtual dye amount of each dye of a bright-field dye group of a case in which the tissue group dyed by using the bright-field dye group including one or more dyes is captured by a transmission-type microscope based on the estimated tissue amount; and generating a virtual transmitted-light image from the estimated dye amount.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 4 is a diagram illustrating a conversion table used when the light quantity of fluorescence is converted to a tissue amount;

FIG. 5 is a diagram illustrating a conversion table used when the tissue amount is converted to a dye amount;

DETAILED DESCRIPTION

Hereinafter, embodiments of an image processing device, an imaging system, an actuation method of the image processing device, and an actuation program of the image processing device according to the disclosure will be described with reference to drawings. Note that the disclosure is not limited by these embodiments. The disclosure can be generally applied to an image processing device which generates a transmitted-light image from a fluorescent image, an imaging system, an actuation method of the image processing device, and an actuation program of the image processing device.

Also, in description of the drawings, same or corresponding elements are appropriately denoted by same reference signs. Also, the drawings are schematic, and it should be noted that dimensional relations of elements, ratios of elements, etc. may be different from reality. Even mutually among the drawings, a part in which mutual dimensional relations or ratios are different may be included.

First Embodiment

Figure 1:
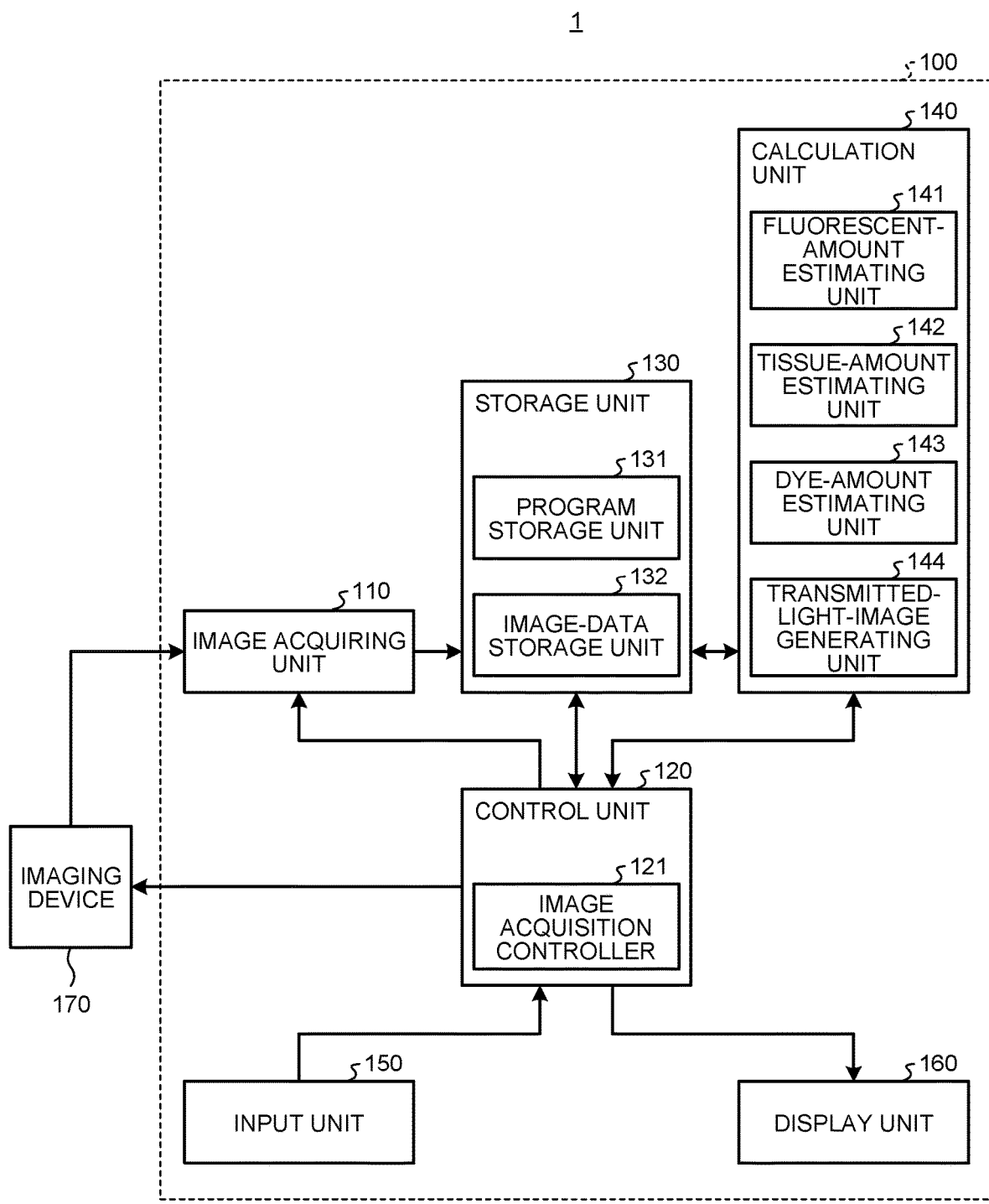
FIG. 1 is a block diagram illustrating a configuration example of an imaging system according to a first embodiment of the disclosure.

FIG. 1 is a block diagram illustrating a configuration example of an imaging system according to a first embodiment of the disclosure. As illustrated in FIG. 1, an imaging system 1 according to the present first embodiment includes an imaging device 170 such as a fluorescent microscope and an image processing device 100, which includes a computer such as a personal computer which is connectable to the imaging device 170.

The image processing device 100 is provided with an image acquiring unit 110, which acquires image data from the imaging device 170; a control unit 120, which controls operation of a whole system including the image processing device 100 and the imaging device 170; a storage unit 130, which stores image data, etc. acquired by the image acquiring unit 110; a calculation unit 140, which executes predetermined image processing based on the image data stored in the storage unit 130; an input unit 150; and a display unit 160.

The image acquiring unit 110 is appropriately constituted depending on a mode of the system including the image processing device 100. For example, in a case in which the imaging device 170 is connected to the image processing device 100, the image acquiring unit 110 is constituted of an interface, which takes in the image data output from the imaging device 170. Also, in a case in which a server for saving the image data generated by the imaging device 170 is installed, the image acquiring unit 110 is constituted of a communication device or the like connected to the server and acquires the image data by carrying out data communication with the server. Alternatively, the image acquiring unit 110 may be constituted of a reader device which detachably attaches a portable-type recording medium and reads the image data recorded in the recording medium.

The control unit 120 is constituted by using a general-purpose processor such as a central processing unit (CPU) or a dedicated processor such as a various calculation circuit which executes a particular function like an application specific integrated circuit (ASIC) or the like. If the control unit 120 is a general-purpose processor, instructions, data transfers, etc. with respect to units constituting the image processing device 100 are carried out by reading various programs stored in the storage unit 130 to integrate and control operation of the entire image processing device 100. Also, if the control unit 120 is a dedicated processor, the processor may independently execute various processing, or various processing may be executed by cooperation or combination of the processor and the storage unit 130 by using various data, etc. stored in the storage unit 130.

The control unit 120 has an image acquisition controller 121, which controls operation of the image acquiring unit 110 and the imaging device 170 to acquire images, and controls operation of the image acquiring unit 110 and the imaging device 170 based on input signals input from the input unit 150, images input from the image acquiring unit 110, and programs, data, etc. stored in the storage unit 130.

The storage unit 130 is constituted of, for example, an IC memory of various types like a read only memory (ROM) or a random access memory (RAM) such as a flash memory which can be updated and recorded, a hard disk which is built in or connected by a data communication terminal, or an information storage device such as a DVD-ROM and an information writing/reading device for the information storage device. The storage unit 130 is provided with a program storage unit 131, which stores an image processing program, and an image-data storage unit 132, which stores the image data, various parameters, etc. used during execution of the image processing program.

The calculation unit 140 is constituted by using a general-purpose processor such as a CPU or a graphics processing unit (GPU) or a dedicated processor such as a various calculation circuit which executes a particular function like an ASIC or the like. If the calculation unit 140 is a general-purpose processor, image processing of estimating a depth at which a particular tissue is present is executed based on a multiband image by reading the image processing program stored in the program storage unit 131. Also, if the calculation unit 140 is a dedicated processor, the processor may independently execute various processing, or image processing may be executed by cooperation or combination of the processor and the storage unit 130 by using various data, etc. stored in the storage unit 130.

In detail, the calculation unit 140 is provided with a fluorescent-amount estimating unit 141, a tissue-amount estimating unit 142, a dye-amount estimating unit 143, and a transmitted-light-image generating unit 144.

The fluorescent-amount estimating unit 141 estimates the light quantity of fluorescence emitted by each fluorescent dye of a fluorescent dye group at each pixel included in a fluorescent image obtained by capturing, by a fluorescent microscope, a tissue group including one or more tissues dyed by using the fluorescent dye group including the one or more fluorescent dyes. The fluorescent dye group is, for example, Hoechst and eosin, respectively dye cell nuclei and cytoplasm, which are tissue groups. However, the fluorescent dye group may be Acridine Orange, Acridine Yellow, or the like, and cell membranes, red blood cells, fibers, mucus, fat, etc. may be dyed as tissues. Also, in a case in which immunostaining is carried out, the fluorescent dye group may be avidin or the like, which may dye tumor cells or the like as tissues.

The tissue-amount estimating unit 142 estimates a tissue amount of each tissue of the tissue group based on the light quantity estimated by the fluorescent-amount estimating unit 141. Specifically, the tissue-amount estimating unit 142 estimates the tissue amounts of the cell nuclei and the cytoplasm from each pixel.

Based on the tissue amount estimated by the tissue-amount estimating unit 142, the dye-amount estimating unit 143 estimates a virtual dye amount of each dye of a bright-field dye group of a case in which a tissue group dyed by using the bright-field dye group including the one or more dyes is captured by a transmission-type microscope. The bright-field dye group is, for example, hematoxylin and eosin, and the dye amounts of hematoxylin and eosin are estimated respectively from cell nuclei and cytoplasm. However, the dye amount of a case in which Masson trichrome stain is carried out may be estimated by a bright-field dye group including aniline or the like. Also, the dye amount of a case in which Giemsa stain, which is special stain, or a Diamino Benzidine (DAB) method, which is immunostaining, is carried out with the bright-field dye group may be estimated.

The transmitted-light-image generating unit 144 generates a virtual transmitted-light image from the dye amount estimated by the dye-amount estimating unit 143. Specifically, the transmitted-light-image generating unit 144 generates a transmitted-light image by synthesizing the dye amounts of hematoxylin and eosin estimated by the dye-amount estimating unit 143.

The input unit 150 is constituted of, for example, various input devices such as a keyboard, a mouse, a touch panel, and various switches and outputs input signals corresponding to operated input to the control unit 120.

The display unit 160 is realized by a display device such as a liquid crystal display (LCD), an electro luminescence (EL) display, or a cathode ray tube (CRT) display and displays various screens based on display signals input from the control unit 120.

The imaging device 170 includes, for example, an imaging element such as a charge coupled device (CCD) or a complementary metal oxide semiconductor (CMOS), and the imaging device converts the light, which has entered a light receiving surface of the imaging element, to an electric signal corresponding to the intensity of the light and outputs that as image data under control of the image acquiring unit 110 of the image processing device 100. Note that the imaging device 170 may be provided with an RGB camera and may capture RGB images or may capture multiband images. Multiband image capturing includes a method of changing the wavelength of illumination light, a method of providing a filter on an optical path of the light from a light source which is white light and changing the wavelength of transmitting light, and a method in which a multicolor sensor is used. The method in which the filter is provided on the optical path includes a method in which a plurality of bandpass filters which allow transmission of different wavelengths is used, a method in which diffraction grating is used, and a method in which a wavelength-variable filter using liquid crystal or sound is used. Also, the light path may be branched and received at the same time by a plurality of cameras having different spectral characteristics.

Figure 2:
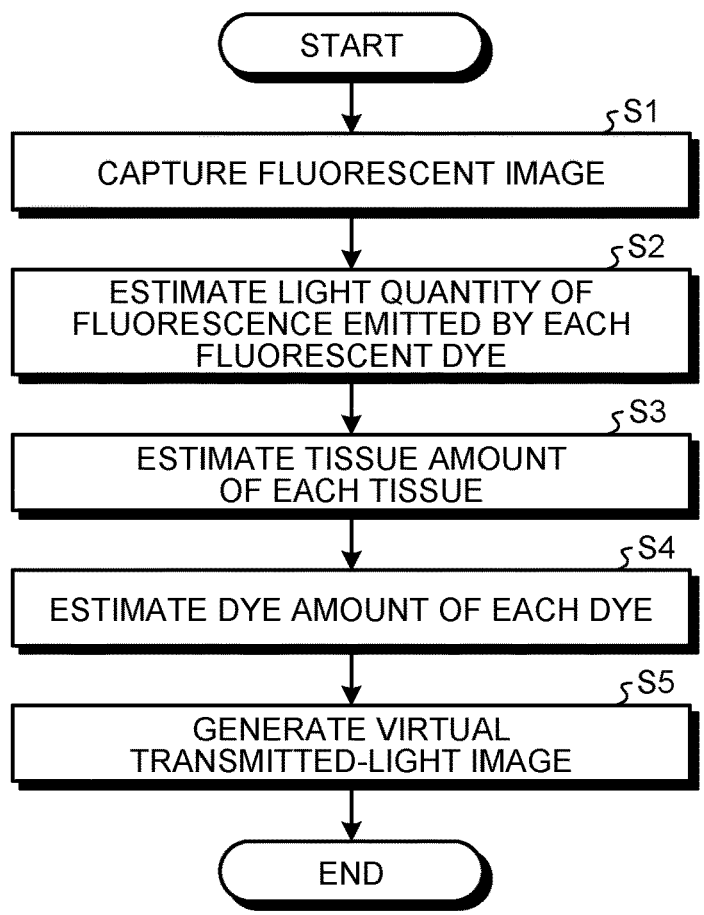
FIG. 2 is a flow chart illustrating operation of the imaging system.

Next, processing of generating a virtual transmitted-light image by using the imaging system according to the present first embodiment will be described. FIG. 2 is a flow chart illustrating operation of the imaging system. As illustrated in FIG. 2, first, the image processing device 100 images a fluorescent image of an object by operating the imaging device 170 under control of the image acquisition controller 121 (step S1). In the present first embodiment, an example in which the fluorescent image is captured in a state in which cell nuclei and cytoplasm, which are tissue groups, are dyed respectively by using Hoechst and eosin as fluorescent dye groups will be described.

Subsequently, the fluorescent-amount estimating unit 141 estimates the light quantity of fluorescence emitted respectively by Hoechst and eosin at each pixel included in the captured fluorescent image (step S2). First, a pixel value $c_f$ of each pixel in the fluorescent image can be expressed as following Formula (4) by using a camera sensitivity characteristic c, a fluorescence spectrum $s_f$, and noise n.

$$c_f(x,y,b)=\int c(b,\lambda)\cdot s_f(x,y,\lambda)d\lambda+n(b) \quad (4)$$

Furthermore, if Formula (4) is expressed by a matrix, following Formula (5) is obtained.

$$C_f(x,y)=CS_f(x,y)+N \quad (5)$$

A Wiener estimation matrix W is following Formula (6) using an autocorrelation matrix $R_{ss}$ of a sample fluorescence spectrum and an autocorrelation matrix $R_{NN}$ of noise.

$$W=R_{ss}\cdot C^t(C\cdot R_{ss}\cdot C^t+R_{NN})^{-1} \quad (6)$$

Therefore, the fluorescence spectrum $S_f$ can be obtained by following Formula (7) by using the Wiener estimation matrix W.

$$S_f(x,y)=W\cdot C_f(x,y) \quad (7)$$

Subsequently, the fluorescence spectrum $s_f$ can be expressed as following Formula (8) by using a reference spectrum $b_f$ of fluorescent dye and a light quantity $a_f$ of the fluorescence.

$$s_f(x, y, \lambda) = \sum_{i=1}^{n} (b_f(i, \lambda) \cdot a_f(x, y, i)) \quad (8)$$

Figure 3:
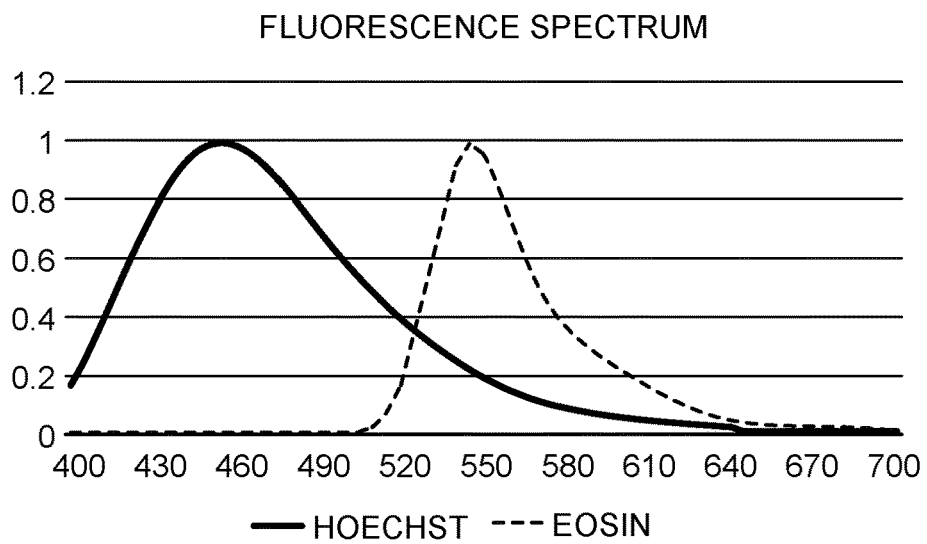
FIG. 3 is a diagram illustrating reference spectra of fluorescent dyes.

FIG. 3 is a diagram illustrating reference spectra of fluorescent dyes. As illustrated in FIG. 3, the reference spectra $b_f$ of Hoechst and eosin are already known. Therefore, i=1 for Hoechst and i=2 for eosin are applied to Formula (8), the light quantities of the fluorescence caused by Hoechst and eosin can be obtained, respectively.

Furthermore, when Formula (8) is expressed by a matrix, following Formula (9) is obtained.

$$S_f(x,y) = B_f A_f(x,y) \quad (9)$$

A pseudo-inverse matrix $P_f$ of the reference spectrum $b_f$ of the fluorescent dye is following Formula (10).

$$P_f = (B_f^T \cdot B_f)^{-1} \cdot B_f^T \quad (10)$$

Therefore, a light quantity $A_f$ of fluorescence can be obtained by following Formula (11) by using the pseudo-inverse matrix $P_f$.

$$A_f(x,y) = P_f S_f(x,y) \quad (11)$$

Specifically, the light quantities of fluorescence of Hoechst and eosin can be obtained, respectively, by Formula (11).

Then, the tissue-amount estimating unit 142 estimates a tissue amount of each tissue of the tissue group based on the light quantity estimated by the fluorescent-amount estimating unit 141 (step S3). A tissue amount $T_n$ of the cell nuclei and a tissue amount $T_c$ of the cytoplasm can be obtained by following Formulas (12) and (13) by using a light quantity $F_h$ of fluorescence of Hoechst, a light quantity $F_e$ of fluorescence of eosin, a coefficient $k_{hn}$, a coefficient $k_{en}$, a coefficient $k_{hc}$, and a coefficient $k_{ec}$.

$$T_n = k_{hn} \cdot F_h + k_{en} \cdot F_e \quad (12)$$

$$T_c = k_{hc} \cdot F_h + k_{ec} \cdot F_e \quad (13)$$

FIG. 4 is a diagram illustrating a conversion table used when the light quantity of fluorescence is converted to a tissue amount. As illustrated in FIG. 4, a coefficient $k_{hn}$=1.00, $k_{en}$=0.00, a coefficient $k_{hc}$=0.00, and a coefficient $k_{ec}$=1.00. In this manner, by connecting the light quantity of one fluorescent dye with the plurality of tissue amounts, a transmitted-light image which is further close to an actually captured image can be generated from the fluorescent image.

Furthermore, the dye-amount estimating unit 143 estimates each of the virtual dye amounts of hematoxylin and eosin of a case in which each of cell nuclei and cytoplasm dyed by using hematoxylin and eosin as bright-field dye groups is captured by using a transmission-type microscope (step S4). A dye amount $D_h$ of hematoxylin and a dye amount $D_e$ of eosin can be obtained by following Formulas (14) and (15) by using the tissue amount $T_n$ of the cell nuclei, the tissue amount $T_c$ of the cytoplasm, the coefficient $k_{hn}$, the coefficient $k_{en}$, the coefficient $k_{hc}$, and the coefficient $k_{ec}$.

$$D_h = k_{nh} \cdot T_n + k_{ch} \cdot T_c \quad (14)$$

$$D_e = k_{ne} \cdot T_n + k_{ce} \cdot T_c \quad (15)$$

FIG. 5 is a diagram illustrating a conversion table used when the tissue amount is converted to a dye amount. As illustrated in FIG. 5, a coefficient $k_{hn}$=1.50, $k_{en}$=2.00, a coefficient $k_{hc}$=0.15, and a coefficient $k_{ec}$=2.00. In this manner, by connecting the one tissue amount with the dye amounts of the plurality of dyes, a transmitted-light image which is further close to an actually captured image can be generated from the fluorescent image.

Figure 6:
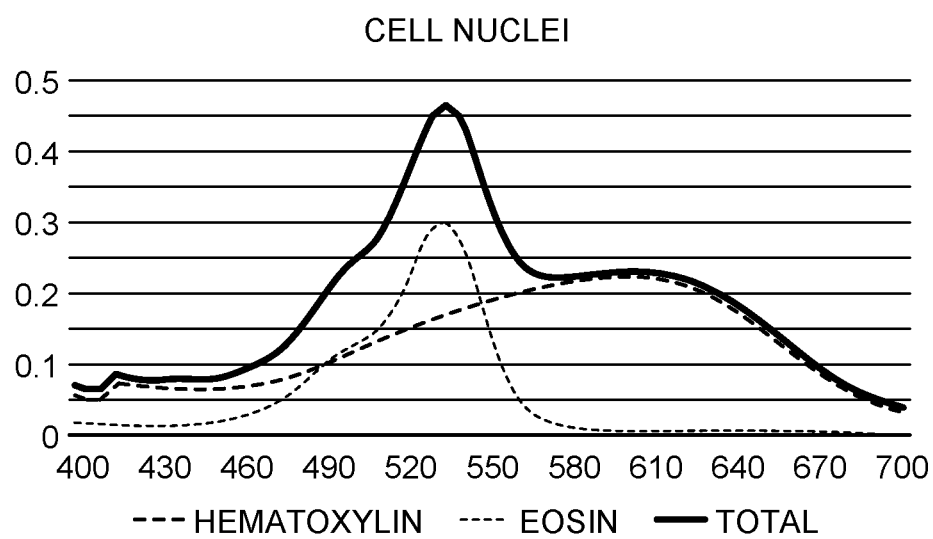
FIG. 6 is a diagram illustrating a state of converting the tissue amount of cell nuclei to a dye amount.
Figure 7:
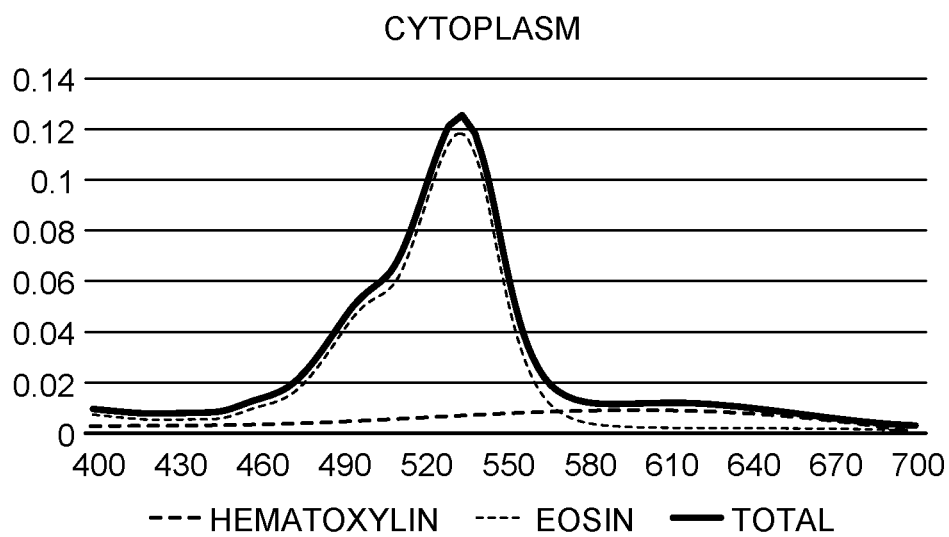
FIG. 7 is a diagram illustrating a state of converting the tissue amount of the cytoplasm to the dye amount.

FIG. 6 is a diagram illustrating a state of converting the tissue amount of the cell nuclei to the dye amount. FIG. 7 is a diagram illustrating a state of converting the tissue amount of the cytoplasm to the dye amount. As illustrated in FIG. 6 and FIG. 7, the tissue amount can be appropriately converted to the dye amount by appropriately setting the coefficient $k_{hn}$, the coefficient $k_{en}$, the coefficient $k_{hc}$, and the coefficient $k_{ec}$.

Subsequently, the transmitted-light-image generating unit 144 generates a virtual transmitted-light image from the dye amount estimated by the dye-amount estimating unit 143 (step S5). Specifically, the transmitted-light-image generating unit 144 synthesizes the dye amounts estimated by the dye-amount estimating unit 143 to generate the virtual transmitted-light image. First, a virtual absorbance spectrum $s_a$ depending on each dye can be expressed as following Formula (16) by using a reference spectrum $b_a$ of the dye in absorbance space and a dye amount $d_a$ of each dye.

$$s_a(x,y,i,\lambda) = b_a(i,\lambda) \cdot d_a(x,y,i) \quad (16)$$

Therefore, the absorbance spectrum $s_a$ depending on all the dyes is following Formula (17).

$$s_a(x, y, \lambda) = \sum_{i=1}^{m} s_a(x, y, i, \lambda) \quad (17)$$

Figure 8:
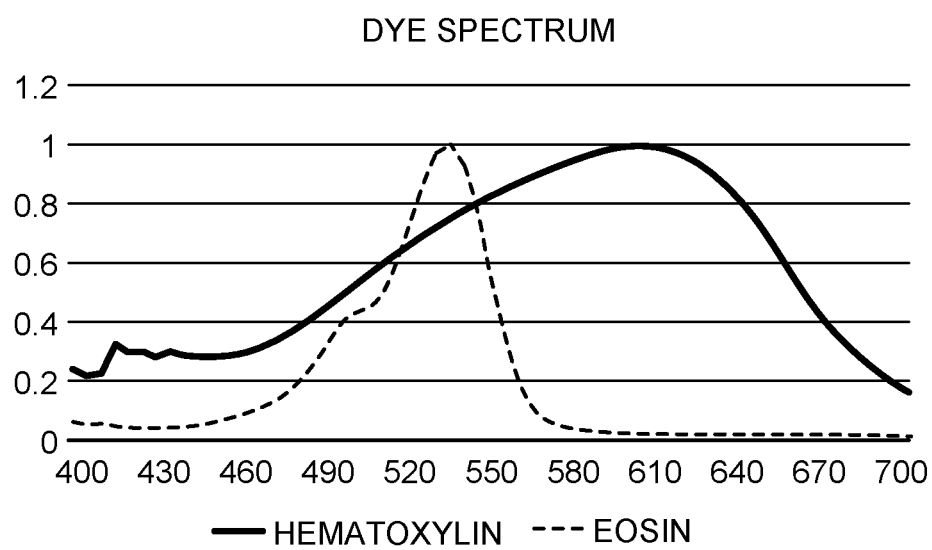
FIG. 8 is a diagram illustrating reference spectra of dyes.

FIG. 8 is a diagram illustrating reference spectra of dyes. As illustrated in FIG. 8, the reference spectra $b_a$ of hematoxylin and eosin are already known. Therefore, i=1 for hematoxylin and i=2 for eosin are applied to Formula (17), the absorbance spectra depending on hematoxylin and eosin can be obtained, respectively.

Then, a virtual transmission $s_t$ can be expressed as following Formula (18).

$$s_t(x,y,\lambda) = e^{-s_a(x,y,\lambda)} \quad (18)$$

Figure 9:
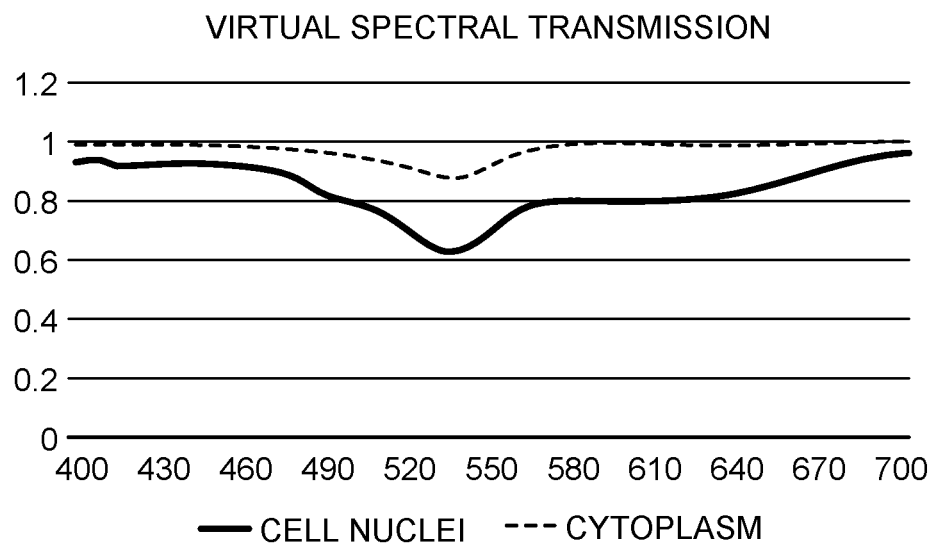
FIG. 9 is a diagram illustrating virtual spectral transmissions.

FIG. 9 is a diagram illustrating virtual spectral transmissions. As illustrated in FIG. 9, the virtual spectral transmissions of the cell nuclei and cytoplasm can be obtained by using Formula (18).

Furthermore, a RAW image, which is a virtual transmitted-light image, can be expressed as following Formula (19) by using the camera sensitivity characteristic c and a spectrum l of illumination.

$$C_{linear}(x,y,b) = \int c(b,\lambda) \cdot l(\lambda) \cdot s_t(x,y,\lambda) d\lambda \quad (19)$$

Also, a sRGB image may be generated as the virtual transmitted-light image. First, XYZ can be expressed as following Formulas (20) to (22), wherein f is a color-matching function.

$$X(x,y) = \int s_t(x,y,\lambda) \cdot f_x(\lambda) \cdot f_x(\lambda) d\lambda \quad (20)$$

$$Y(x,y) = \int s_t(x,y,\lambda) \cdot f_y(\lambda) d\lambda \quad (21)$$

$$Z(x,y) = \int s_t(x,y,\lambda) \cdot f_Z(\lambda) d\lambda \quad (22)$$

Then, $sRGB_{linear}$ can be calculated by following Formula (23).

$$\begin{bmatrix} R_{linear}(x,y) \\ G_{linear}(x,y) \\ B_{linear}(x,y) \end{bmatrix} = \begin{bmatrix} 3.2406 & -1.5372 & -0.4986 \\ -0.9689 & 1.8758 & 0.0415 \\ 0.0557 & -0.2040 & 1.0570 \end{bmatrix} \begin{bmatrix} X(x,y) \\ Y(x,y) \\ Z(x,y) \end{bmatrix} \quad (23)$$

Furthermore, a non-linear sRCG image can be generated by calculating $C_{srgb}(x,y,b) = 12.96 \cdot C_{linear}(x,y,b)$ in a case of $C_{linear}(x,y,b) \leq 0.0031308(x,y,b)$ and calculating $C_{srgb}(x,y,b) = 1.055 \cdot C_{linear}(x,y,b)^{1/24} - 0.055$ in a case of $C_{linear}(x,y,b) > 0.0031308$.

Then, the generated transmitted-light image is displayed by the display unit 160 under control of the control unit 120, and the series of processing is finished.

As described above, according to the first embodiment, the tissues are interposed when the transmitted-light image is generated from the fluorescent image, and, as a result, the transmitted-light image which is highly accurate and faithfully expressing dye characteristics of a pathological specimen can be generated. Since a pathologist is generally used to observation of transmitted-light images, observation is facilitated by converting a fluorescent image to a transmitted-light image.

Note that the fluorescent image and the transmitted-light image may be displayed by switching or in juxtaposition by the display unit 160 under control of the control unit 120. Comparison between the fluorescent image and the transmitted-light image can be facilitated, and confirmation whether the transmitted-light image is appropriate or not can be facilitated.

Note that the calculation methods are not limited to those described above. Calculations can be carried out by appropriately combining the above described calculation methods and below-described calculation methods. The light quantity of the fluorescence of each fluorescent dye may be directly estimated from the fluorescent image based on a fluorescence-amount estimation matrix. The fluorescence-amount estimation matrix may be theoretically calculated or may be obtained from the product of a spectrum estimation matrix and a fluorescence-amount estimation matrix.

Also, the fluorescence-amount estimation matrix may also be statistically calculated. Specifically, pairs of pixel values and light quantities of fluorescence are calculated from each of a plurality of fluorescence spectra. Then, an estimation matrix (regression matrix), which regresses from the pixel values to the light quantities of fluorescence, is calculated from the data of plurality of pairs of the pixel values and the light quantities of fluorescence. The regression matrix can be obtained by a pseudo-inverse matrix.

Also, the light quantity of the fluorescence of each fluorescent dye may be directly calculated from the fluorescent image based on a look-up table. Specifically, pairs of pixel values and light quantities of fluorescence are calculated from each of a plurality of fluorescence spectra. Then, the look-up table for referencing the light quantities of fluorescence from the pixel values can be created from the data of plurality of pairs of the pixel values and the light quantities of fluorescence.

Also, the light quantity of the fluorescence of each fluorescent dye may be directly estimated from the fluorescent image by using machine learning. Specifically, the light quantity of fluorescence of each pixel is calculated from a plurality of fluorescent images by using any of the above described methods. Then, a model which estimates light quantities of fluorescence from pixel values is learned from data of a plurality of pairs of fluorescent images and fluorescence-amount images. Also, a model may be learned by using deep learning.

Also, based on a pixel-value calculating matrix, a virtual transmitted-light image may be calculated directly from virtual dye amounts. Specifically, the pixel value of each pixel of the virtual transmitted-light image is calculated based on the above described method from a plurality of virtual dye amounts. Then, an estimation matrix (regression matrix), which regresses from the virtual dye amounts to the pixel values, from the data of a plurality of pairs of the virtual dye amounts and the virtual pixel values. The regression matrix may be a polynomial approximation.

Also, based on a look-up table, a virtual transmitted-light image may be calculated directly from virtual dye amounts. Specifically, the pixel value of each pixel of the virtual transmitted-light image is calculated based on the above described method from a plurality of virtual dye amounts. Then, the look-up table for referencing the virtual pixel values from the virtual dye amounts can be created from the data of a plurality of pairs of the virtual dye amounts and the virtual pixel values.

Also, by using machine learning, a virtual transmitted-light image may be calculated directly from virtual dye amounts. Specifically, the pixel value of each pixel of the virtual transmitted-light image is calculated based on the above described method from a plurality of virtual dye amounts. Then, a model which estimates the virtual pixel values from the virtual dye amounts is learned from the data of a plurality of pairs of the virtual dye amounts and the virtual pixel values. Also, the model may be learned by deep learning.

Second Embodiment

Figure 10:
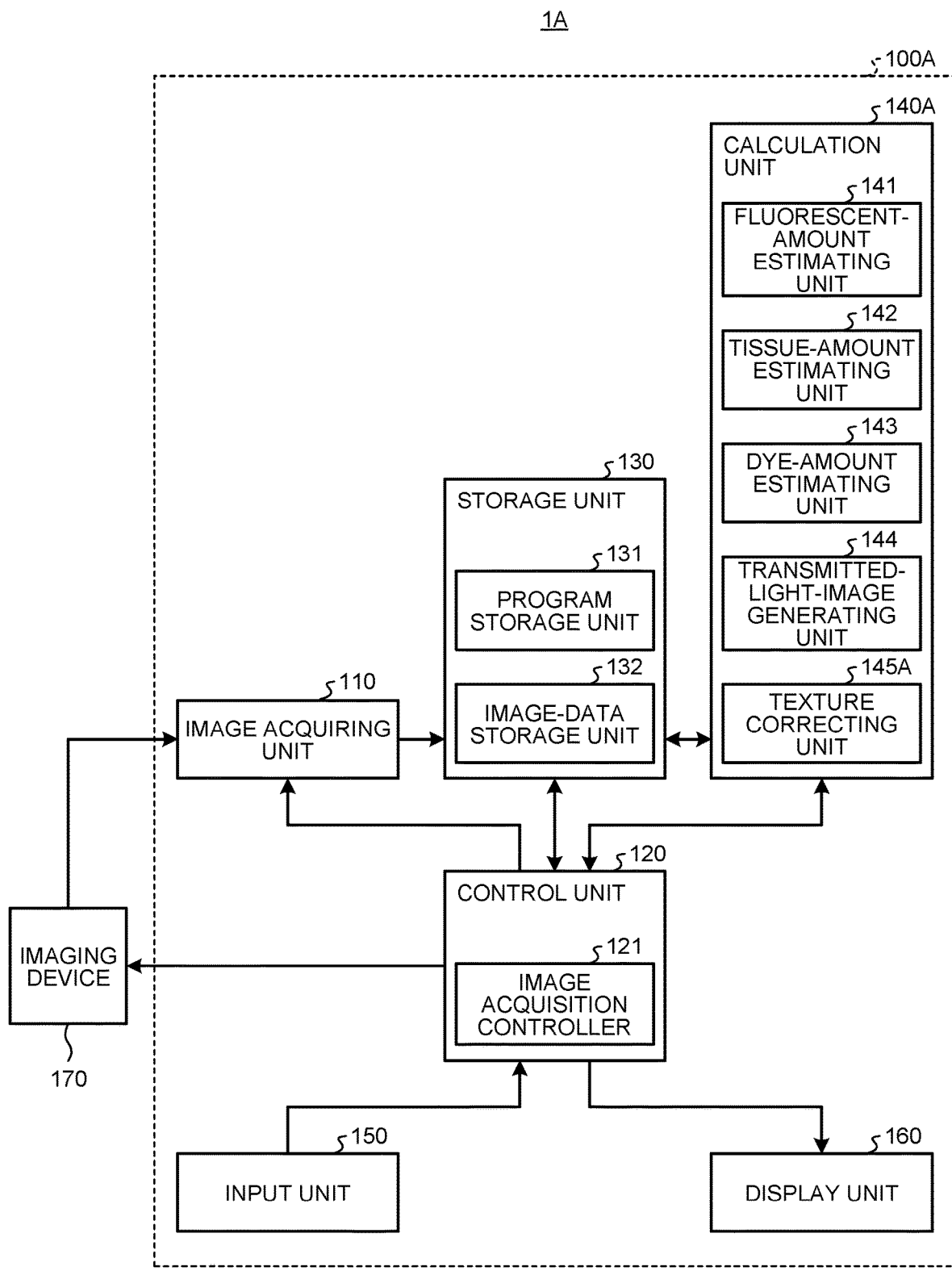
FIG. 10 is a block diagram illustrating a configuration example of an imaging system according to a second embodiment of the disclosure.

Next, a second embodiment of the disclosure will be described. FIG. 10 is a block diagram illustrating a configuration example of an imaging system according to the second embodiment of the disclosure. As illustrated in FIG. 10, in an imaging system 1A, a calculation unit 140A of an image processing device 100A is provided with a texture correcting unit 145A as an image correcting unit, which corrects any of images including fluorescent images, fluorescence-amount images generated based on the light quantities estimated by the fluorescent-amount estimating unit 141, tissue-amount images generated based on the tissue amounts estimated by the tissue-amount estimating unit 142, dye-amount images generated based on the dye amounts estimated by the dye-amount estimating unit 143, and transmitted-light images. As a result, according to the second embodiment, texture of a focal depth which is equivalent to that in transmitted-light observation can be reproduced in a virtual transmitted-light image generated from a fluorescent image. Therefore, according to the second embodiment, a more accurate transmitted-light image can be generated.

Third Embodiment

Figure 11:
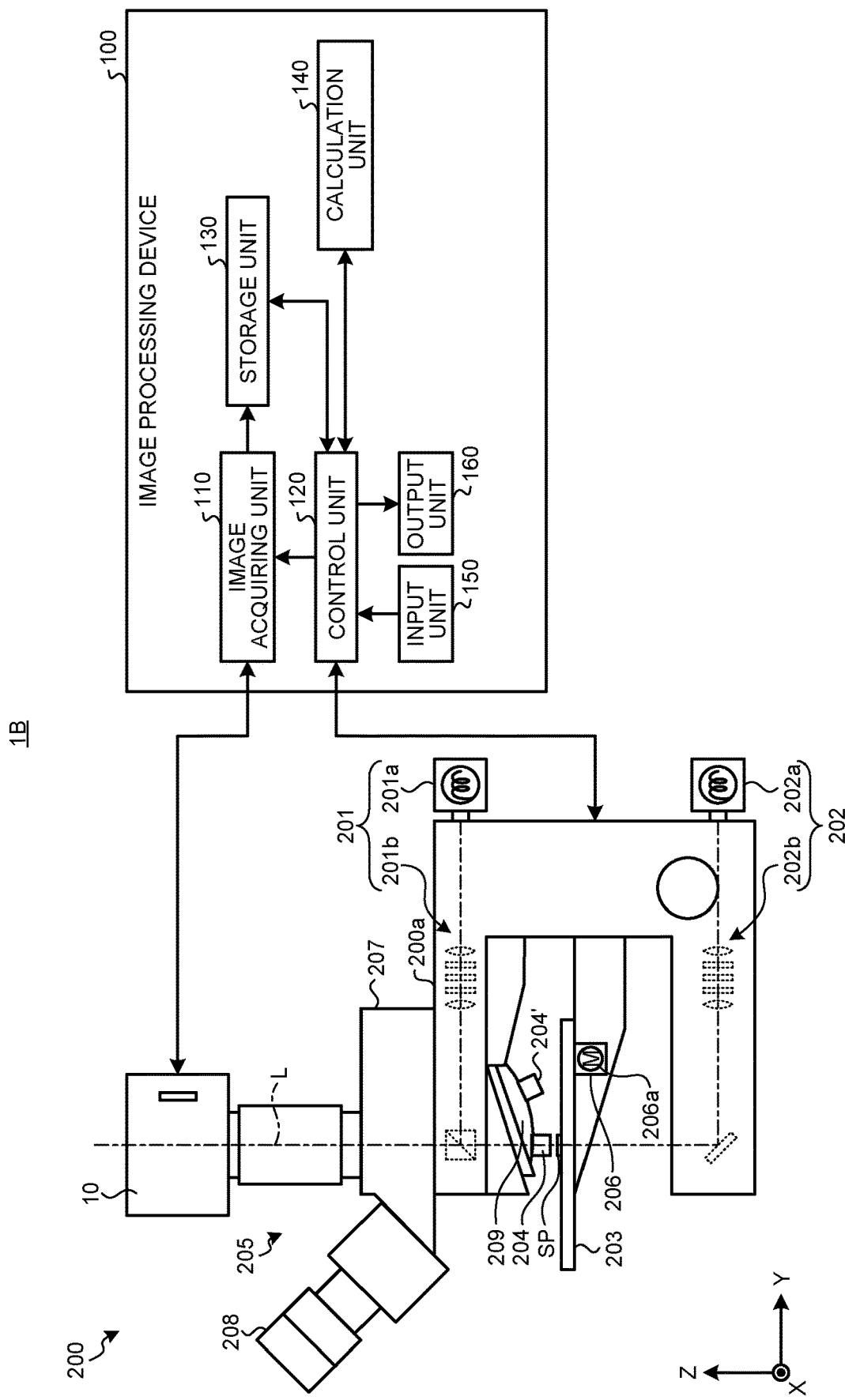
FIG. 11 is a diagram illustrating a configuration example of an imaging system according to a third embodiment of the disclosure.

Next, a third embodiment of the disclosure will be described. FIG. 11 is a diagram illustrating a configuration example of an imaging system according to the third embodiment of the disclosure. As illustrated in FIG. 11, an imaging system 1B according to the present third embodiment is provided with a microscope device 200, which is provided with an imaging device 170, and an image processing device 100. Note that, instead of the image processing device 100, the image processing device 100A illustrated in FIG. 10 may be provided.

The microscope device 200 has an approximately-C-shaped arm 200a provided with an incident-light illumination unit 201 and a transmitted-light illumination unit 202, a specimen stage 203 attached to the arm 200a and on which an object SP serving as an observation target is placed, an objective lens 204 provided in a first end side of a lens tube 205 via a trinocular-lens-tube unit 207 so as to be opposed to the specimen stage 203, and a stage-position changing unit 206 which moves the specimen stage 203. The trinocular-lens-tube unit 207 branches observation light of the object SP, which has entered from the objective lens 204, into the imaging device 170, which is provided in a second end side of the lens tube 205, and an eyepiece unit 208. The eyepiece unit 208 is for a user to directly observe the object SP.

The incident-light illumination unit 201 is provided with an incident-light-illumination light source 201a and an incident-light-illumination optical system 201b and irradiates the object SP with incident-light illumination. The incident-light-illumination optical system 201b includes various optical members (filter unit, shutter, field stop, aperture diaphragm, etc.), which condenses the illumination light emitted from the incident-light-illumination light source 201a and guide the light in a direction of an observation optical path L.

The transmitted-light illumination unit 202 is provided with a transmitted-light-illumination light source 202a and a transmitted-light-illumination optical system 202b and irradiates the object SP with transmitted-light illumination light. The transmitted-light-illumination optical system 202b includes various optical members (filter unit, shutter, field stop, aperture diaphragm, etc.), which condenses the illumination light emitted from the transmitted-light-illumination light source 202a and guide the light in a direction of the observation optical path L.

The objective lens 204 is attached to a revolver 209, which can retain a plurality of objective lenses (for example, objective lenses 204, 204') having mutually different magnifications. The imaging magnification can be changed by rotating this revolver 209 and changing the objective lenses 204, 204' opposed to the specimen stage 203.

In the lens tube 205, a plurality of zoom lenses and a zoom unit, which includes a drive unit which changes the positions of these zoom lenses, are provided. The zoom unit magnifies or demagnifies an object image in an imaging view field by adjusting the positions of the zoom lenses.

The stage-position changing unit 206 includes the drive unit 206a such as a stepping motor and changes the imaging view field by moving the position of the specimen stage 203 within an XY plane. Also, the stage-position changing unit 206 adjusts a focal point of the objective lens 204 to the object SP by moving the specimen stage 203 along a Z-axis.

When a magnified image of the object SP generated in the microscope device 200 like this is subjected to multiband imaging in the imaging device 170, a color image of the object SP is displayed by the display unit 160. Then, the image processing device 100 or the image processing device 100A generates a transmitted-light image and displays the transmitted-light image by the display unit 160.

According to the disclosure, an image processing device, an imaging system, an actuation method of an image processing device, and an actuation program of an image processing device capable of generating a highly accurate transmitted-light image by subjecting a fluorescent image to image processing can be realized.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device comprising:
   a processor comprising hardware, the processor being configured to:
   with respect to each pixel included in a fluorescent image obtained by capturing a tissue group including one or more tissues dyed by using a fluorescent dye group including one or more fluorescent dyes by a fluorescent microscope, estimate a light quantity of fluorescence emitted by each fluorescent dye of the fluorescent dye group;
   estimate a tissue amount of each tissue of the tissue group based on the estimated light quantity;
   estimate a virtual dye amount of each dye of a bright-field dye group of a case in which the tissue group dyed by using the bright-field dye group including one or more dyes is captured by a transmission-type microscope based on the estimated tissue amount; and
   generate a virtual transmitted-light image from the estimated dye amount.

2. The image processing device according to claim 1, wherein the processor is further configured to correct any of images including the fluorescent image, a fluorescence-amount image generated based on the estimated light quantity, a tissue-amount image generated based on the estimated tissue amount, a dye-amount image generated based on the estimated dye amount, and the transmitted-light image.

3. The image processing device according to claim 1, wherein the processor is further configured to
   estimate tissue amounts of a plurality of tissues from each pixel,
   estimate dye amounts of a plurality of dyes from each tissue, and
   synthesize the estimated dye amounts of the plurality of dyes to generate the transmitted-light image.

4. The image processing device according to claim 1, wherein the processor is further configured to
   estimate a light quantity $A_f$ of fluorescence emitted by the fluorescent dye group by following Formula (2) by using a pseudo-inverse matrix $P_f$ calculated by following Formula (1) using a matrix $B_f$ calculated based on a reference spectrum of each fluorescent dye of the fluorescent dye group:

$$A_f(x,y) = P_f \cdot S_f(x,y) \tag{1}$$

$$P_f (B_f^T \cdot B_f)^{-1} \cdot B_f^T \tag{2}$$

5. The image processing device according to claim 1, wherein the processor is further configured to calculate each tissue amount of the tissue group by multiplying the estimated light quantity of fluorescence emitted by each fluorescent dye of the fluorescent dye group by a coefficient determined depending on the fluorescent dye and obtaining a sum.

6. The image processing device according to claim 1, wherein the processor is further configured to calculate each dye amount of the bright-field dye group by multiplying the estimated tissue amount of each tissue of the tissue group by a coefficient determined depending on the tissue and obtaining a sum.

7. The image processing device according to claim 1, wherein processor is further configured to
estimate a virtual transmission $s_t$ of the bright-field dye group by following Formula (3) by using an absorbance spectrum $s_a$ calculated based on a reference spectrum of each dye of the bright-field dye group, and
generate the transmitted-light image based on the transmission $s_t$:

$$s_t(x,y,\lambda)=e^{-s_a(x,y,\lambda)} \quad (3).$$

8. An imaging system comprising:
the image processing device according to claim 1;
an illuminator configured to generate excitation light irradiating a specimen;
an illumination-light optical system configured to illuminate the specimen with the excitation light generated by the illuminator;
an image-forming optical system configured to form an image of the fluorescence from the specimen; and
an imager configured to capture the image of the fluorescence formed by the image-forming optical system.

9. An actuation method of an image processing device, the actuation method comprising:
with respect to each pixel included in a fluorescent image obtained by capturing a tissue group including one or more tissues dyed by using a fluorescent dye group including one or more fluorescent dyes by a fluorescent microscope, estimating a light quantity of fluorescence emitted by each fluorescent dye of the fluorescent dye group;
estimating a tissue amount of each tissue of the tissue group based on the estimated light quantity;
estimating a virtual dye amount of each dye of a bright-field dye group of a case in which the tissue group dyed by using the bright-field dye group including one or more dyes is captured by a transmission-type microscope based on the estimated tissue amount; and
generating a virtual transmitted-light image from the estimated dye amount.

10. A non-transitory computer-readable recording medium with an executable program stored thereon, the program causing an image processing device to execute:
with respect to each pixel included in a fluorescent image obtained by capturing a tissue group including one or more tissues dyed by using a fluorescent dye group including one or more fluorescent dyes by a fluorescent microscope, estimating a light quantity of fluorescence emitted by each fluorescent dye of the fluorescent dye group;
estimating a tissue amount of each tissue of the tissue group based on the estimated light quantity;
estimating a virtual dye amount of each dye of a bright-field dye group of a case in which the tissue group dyed by using the bright-field dye group including one or more dyes is captured by a transmission-type microscope based on the estimated tissue amount; and
generating a virtual transmitted-light image from the estimated dye amount.

\* \* \* \* \*